US010881425B2

(12) United States Patent
Tanigami et al.

(10) Patent No.: US 10,881,425 B2
(45) Date of Patent: Jan. 5, 2021

(54) ULTRASONIC SURGICAL INSTRUMENT AND PROCESSING METHOD FOR ULTRASONIC SURGICAL DEVICE

(71) Applicant: OLYMPUS CORPORATION, Hachioji (JP)

(72) Inventors: Yasuo Tanigami, Hachioji (JP); Moe Goto, Kunitachi (JP); Koji Kimoto, Tachikawa (JP)

(73) Assignee: OLYMPUS CORPORATION, Tokyo (JP)

(*) Notice: Subject to any disclaimer, the term of this patent is extended or adjusted under 35 U.S.C. 154(b) by 123 days.

(21) Appl. No.: 16/145,955

(22) Filed: Sep. 28, 2018

(65) Prior Publication Data

US 2019/0105073 A1 Apr. 11, 2019

Related U.S. Application Data

(63) Continuation of application No. PCT/JP2017/013689, filed on Mar. 31, 2017.

(30) Foreign Application Priority Data

Mar. 31, 2016 (WO) .................. PCT/JP2016/060779

(51) Int. Cl.
*A61B 17/32* (2006.01)
*A61B 17/3205* (2006.01)
(Continued)

(52) U.S. Cl.
CPC .. *A61B 17/320068* (2013.01); *A61B 17/3205* (2013.01); *A61B 2017/00017* (2013.01);
(Continued)

(58) Field of Classification Search
CPC ................ A61B 17/32; A61B 17/3205; A61B 17/320068; A61B 2017/00017;
(Continued)

(56) References Cited

U.S. PATENT DOCUMENTS 4,827,911 A * 5/1989 Broadwin ........ A61B 17/22012
310/17
6,053,906 A 4/2000 Honda et al.
(Continued)

FOREIGN PATENT DOCUMENTS

JP H07-23974 A 1/1995
JP H11-70118 A 3/1999
(Continued)

OTHER PUBLICATIONS

Oct. 2, 2018 International Preliminary Report on Patentability issued in International Patent Application No. PCT/JP2017/013689.
(Continued)

*Primary Examiner* — George J Ulsh
(74) *Attorney, Agent, or Firm* — Oliff PLC (57) ABSTRACT

An ultrasonic surgical instrument includes an ultrasonic transducer configured to vibrate ultrasonically, a probe configured to treat a living tissue by the ultrasonic vibration, a detector configured to detect a pressing force of the probe against the living tissue, a memory configured to store a predetermined value related to a pressing force in accordance with the living tissue, a comparing section configured to compare the pressing force detected by the detector with the predetermined value stored in the memory, and a notification section configured to perform a notification in response to a comparison result obtained by the comparing section.

11 Claims, 10 Drawing Sheets

(51) Int. Cl.
*A61B 90/00* (2016.01)
*A61B 17/00* (2006.01)

(52) U.S. Cl.
CPC ............... *A61B 2017/00026* (2013.01); *A61B 2017/00084* (2013.01); *A61B 2017/00973* (2013.01); *A61B 2017/320073* (2017.08); *A61B 2090/065* (2016.02)

(58) Field of Classification Search
CPC ........... A61B 2017/00026; A61B 2017/00084; A61B 2017/00973; A61B 2017/320073; A61B 2090/065
See application file for complete search history.

(56) References Cited

U.S. PATENT DOCUMENTS

| | | | |
|---|---|---|---|
| 2003/0073987 A1* | 4/2003 | Sakurai | A61B 18/1442 606/28 |
| 2012/0136279 A1 | 5/2012 | Tanaka et al. | |
| 2014/0012299 A1 | 1/2014 | Stoddard et al. | |
| 2017/0042528 A1 | 2/2017 | Ellegala | |
| 2017/0128122 A1* | 5/2017 | Rontal | A61B 17/14 |
| 2017/0165507 A1* | 6/2017 | Tanigami | A61N 7/02 |
| 2018/0185054 A1* | 7/2018 | Murasawa | A61B 17/3205 |
| 2019/0029708 A1* | 1/2019 | Yamada | A61B 17/320068 |
| 2019/0290317 A1* | 9/2019 | Onuma | A61B 17/00 |

FOREIGN PATENT DOCUMENTS

| | | |
|---|---|---|
| JP | 2003-235862 A | 8/2003 |
| JP | 2004-209041 A | 7/2004 |
| JP | 2009-504313 A | 2/2009 |
| WO | 2011/004449 A1 | 1/2011 |
| WO | 2015/164753 A1 | 10/2015 |

OTHER PUBLICATIONS

Jun. 20, 2017 International Search Report issued in International Patent Application No. PCT/JP2017/013689.

Jul. 2, 2019 Office Action issued in Japanese Patent Application No. 2018-509673.

Jul. 3, 2020 Office Action issued in Chinese Patent Application No. 201780021435.6.

* cited by examiner

ULTRASONIC SURGICAL INSTRUMENT AND PROCESSING METHOD FOR ULTRASONIC SURGICAL DEVICE

CROSS-REFERENCE TO RELATED APPLICATIONS

This application is a Continuation Application of PCT Application No. PCT/JP2017/013689, filed Mar. 31, 2017 and based upon and claiming the benefit of priority from the prior Japanese Patent Application No. PCT/JP2016/060779, filed Mar. 31, 2016, the entire contents of both are by reference herein.

BACKGROUND OF THE INVENTION

1. Field of the Invention

The present invention relates to an ultrasonic surgical instrument and a processing method for an ultrasonic surgical device.

2. Description of the Related Art

Ultrasonic surgical instruments are known as one of treatment instruments for treating living tissues. The ultrasonic surgical instrument is configured to treat a living tissue by pressing an ultrasonically vibrating probe against a living tissue as a subject. In order for efficient treatment to be carried out, it is important that pressing is performed with an appropriate pressing force. For this reason, for example, the ultrasonic surgical instrument proposed in Jpn. Pat. Appln. KOKAI Publication No. 2003-235862 detects a pressing force by a spring that causes a mechanical change in response to a pressing force when the probe comes into contact with the living tissue, and a detector that detects a change in the spring, and generates ultrasonic vibration when the detected pressing force is within a desired range.

BRIEF SUMMARY OF THE INVENTION

An ultrasonic surgical instrument according to a first aspect of the present invention includes an ultrasonic transducer configured to vibrate ultrasonically; a probe configured to treat a living tissue by the ultrasonic vibration; a detector configured to detect a pressing force of the probe against the living tissue; a memory configured to store a predetermined value related to a pressing force in accordance with the living tissue; a comparing section configured to compare the pressing force detected by the detector with the predetermined value stored in the memory; and a notification section configured to perform a notification in response to a comparison result by the comparing section.

An ultrasonic surgical instrument according to a second aspect of the present invention includes an ultrasonic transducer configured to vibrate ultrasonically; a probe configured to treat a living tissue by the ultrasonic vibration; a detector configured to detect a pressing force of the probe against the living tissue; a memory configured to store a predetermined value related to a pressing force in accordance with the living tissue; and an output generating section configured to control an amplitude of the ultrasonic vibration generated by the ultrasonic transducer so that the pressing force detected by the detector becomes a predetermined value of a pressing force in accordance with the living tissue.

A processing method for an ultrasonic surgical device according to a third aspect of the present invention includes a step of detecting, by a detector, a pressing force with which a probe transmitting an ultrasonic transducer generated by an ultrasonic transducer is pressed against the living tissue; a step of referring to, by a comparing section, a memory and comparing the pressing force detected in the detecting step with a predetermined value related to a pressing force in accordance with the living tissue stored in the memory; and a step of performing a notification by a notification section in response to a comparison result of the comparing step.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, embodiments of the present invention will be described with reference to the drawings.

First Embodiment

Figure 1:
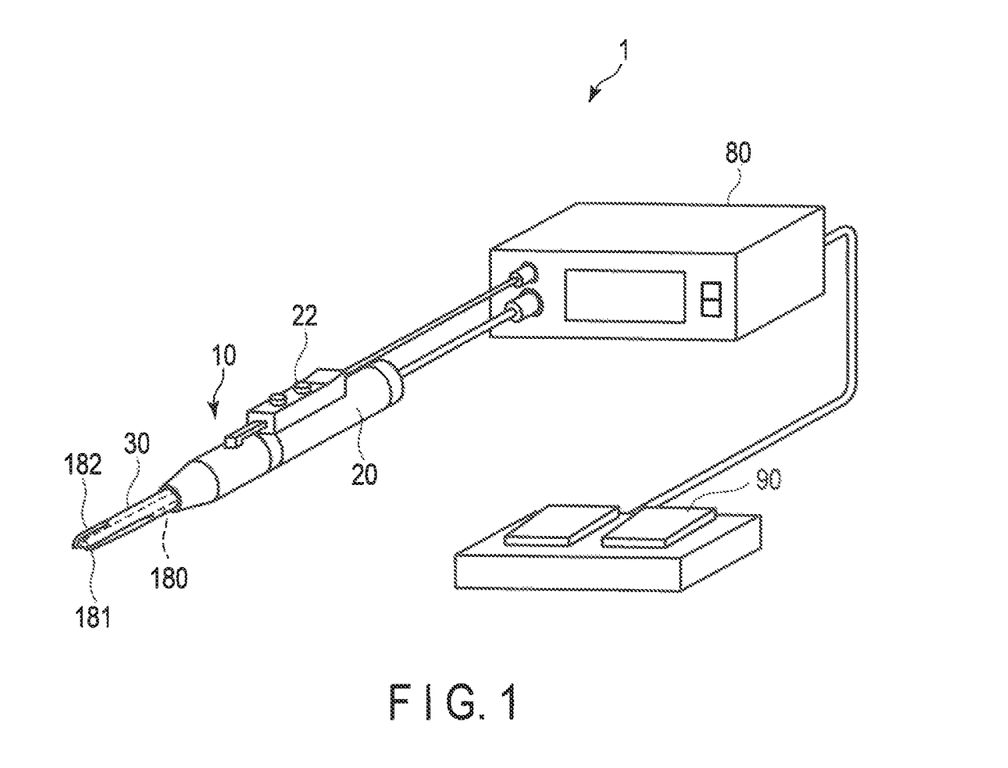
FIG. 1 is a diagram showing the configuration of an ultrasonic surgical system as an example of an ultrasonic surgical instrument according to each embodiment.

A first embodiment of the present invention will be described. FIG. 1 is a diagram showing the configuration of an ultrasonic surgical system 1 as an example of an ultrasonic surgical instrument according to each embodiment of the present invention. The ultrasonic surgical system 1 includes a treatment instrument 10 for performing treatment on a living tissue by ultrasonic waves, a power supply device 80 that supplies driving power to the treatment instrument 10, and a foot switch 90. The ultrasonic surgical system 1 has a cortical bone and cancellous bone excision mode which is a mode suitable for excising hard bone such as cortical bone and a cartilage excision mode which is a mode suitable for excision a cartilage. The ultrasonic surgical system 1, however, can also be used for treatment other than bone excision.

The treatment instrument 10 includes a handpiece 20, a probe 180 protruding from the handpiece 20, and an elongated sheath 30 formed around the probe 180. In the following description, the probe 180 side of the treatment instrument 10 will be referred to as a distal side of the treatment instrument 10, and the handpiece 20 side will be referred to as a proximal side.

The handpiece 20 includes an ultrasonic transducer therein. The ultrasonic transducer vibrates ultrasonically according to the driving power from the power supply device 80. The handpiece 20 transmits the ultrasonic vibration generated by the ultrasonic transducer to the probe 180. The probe 180 is connected to the ultrasonic transducer and vibrates in response to the vibration of the ultrasonic transducer.

The distal end of the sheath 30 is formed in a semi-cylindrical shape, and a treatment portion 181 provided at the distal end of the probe 180 is exposed from the semi-cylindrically formed portion. Furthermore, a cold knife 182 is formed at the distal end of the sheath 30. The cold knife 182, for example, is formed of a corrosion-resistant metallic material and is used to facilitate excision of a living tissue. The cold knife 182 may not be provided.

The handpiece 20 also includes an input section 22. The input section 22 is a section for inputting an instruction for driving the ultrasonic transducer. The input section 22 may include a plurality of switches for switching between a cortical bone/cancellous bone excision mode and a cartilage excision mode. The input section 22 is connected to the power supply device 80. The ultrasonic transducer in the handpiece 20 is connected to the power supply device 80. The power supply device 80 detects an input to the input section 22 and supplies driving power in response to the input to the ultrasonic transducer.

The foot switch 90 has the same function as the input section 22 provided in the handpiece 20. That is, the foot switch 90 may include the plurality of switches for switching between the cortical bone and cancellous bone excision mode and the cartilage excision mode, similarly to the input section 22. Upon detecting an input to the foot switch 90, the power supply device 80 supplies driving power in response to the input to the ultrasonic transducer. It is sufficient that at least one of the input section 22 and the foot switch 90 is provided.

When performing a treatment, a user holds the handpiece 20, and brings a treatment portion 181 provided in the probe 180 that vibrates ultrasonically into contact with a living tissue as a treatment target. At this time, the user operates the input section 22 or the foot switch 90 to vibrate the ultrasonic transducer. Vibrations generated by the ultrasonic transducer are transmitted to the probe 180. The treatment portion 181 of the vibrating probe 180 is brought into contact with the living tissue, whereby a treatment such as excision of a living tissue is performed.

Figure 2:
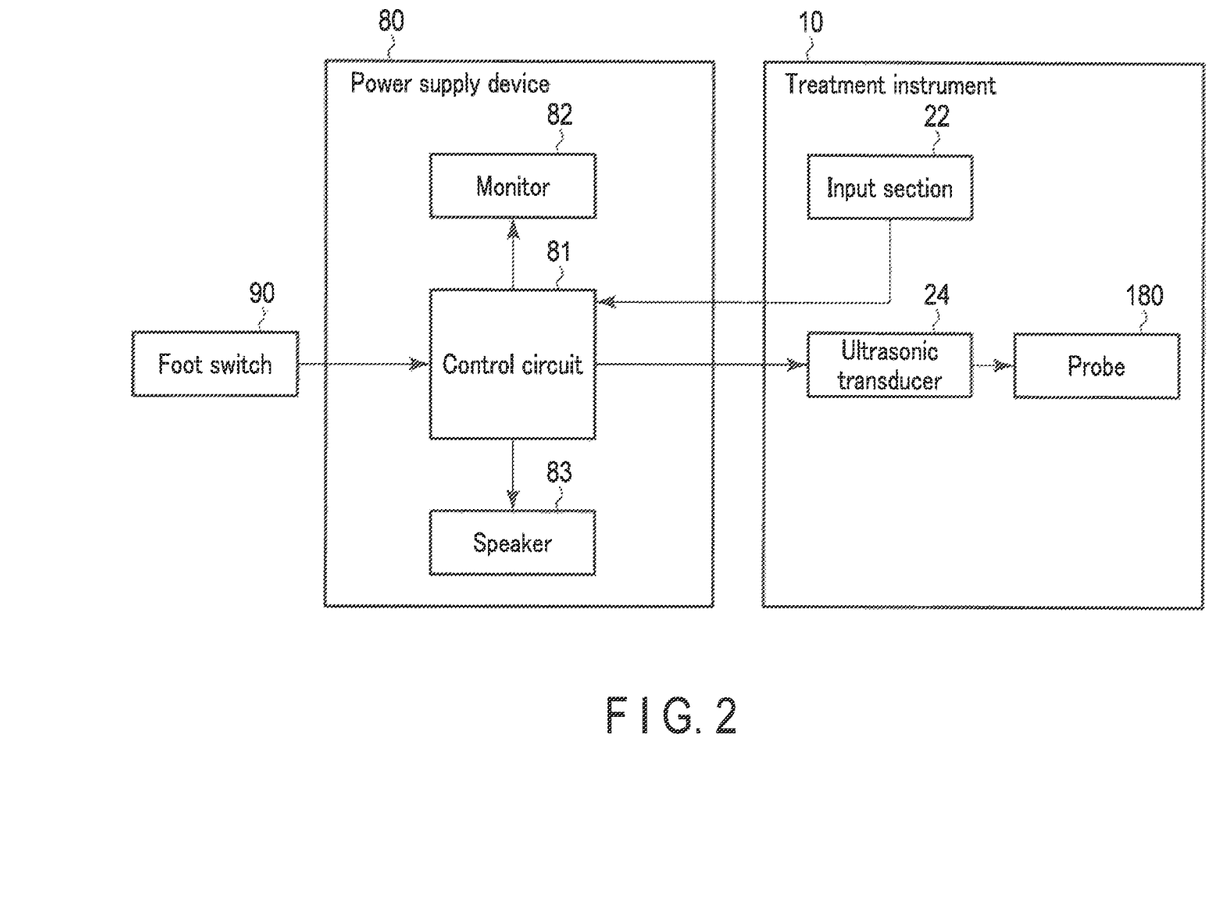
FIG. 2 is a block diagram showing the main configuration of the ultrasonic surgical system according to the first embodiment.

FIG. 2 is a block diagram showing the main configuration of the ultrasonic surgical system 1 according to the first embodiment of the present invention. In FIG. 2, the same reference numerals as those in FIG. 1 denote the same components as those described in FIG. 1, and descriptions thereof will be omitted.

As shown in FIG. 2, the power supply device 80 includes a control circuit 81, a monitor 82, and a speaker 83.

The control circuit 81 is configured, for example, as an IC including an output generating circuit configured to generate driving power, for example, of an ultrasonic transducer 24, and a circuit configured to notify an operator whether or not the pressing of the probe 180 by the operator is appropriate. The control circuit 81 controls the driving power of the ultrasonic transducer 24 in response to the input from the input section 22 or the foot switch 90. Furthermore, the control circuit 81 detects the pressing force of the probe 180 by the operator against a living tissue as a subject and notifies the operator whether or not the current pressing of the probe 180 is appropriate in response to the detected pressing force, for example, by using the monitor 82, using the speaker 83, or using both of them.

The monitor 82 is, for example, a liquid crystal display, and displays various images based on control by the control circuit 81. The speaker 83 emits various sounds under the control of the control circuit 81.

Figure 3:
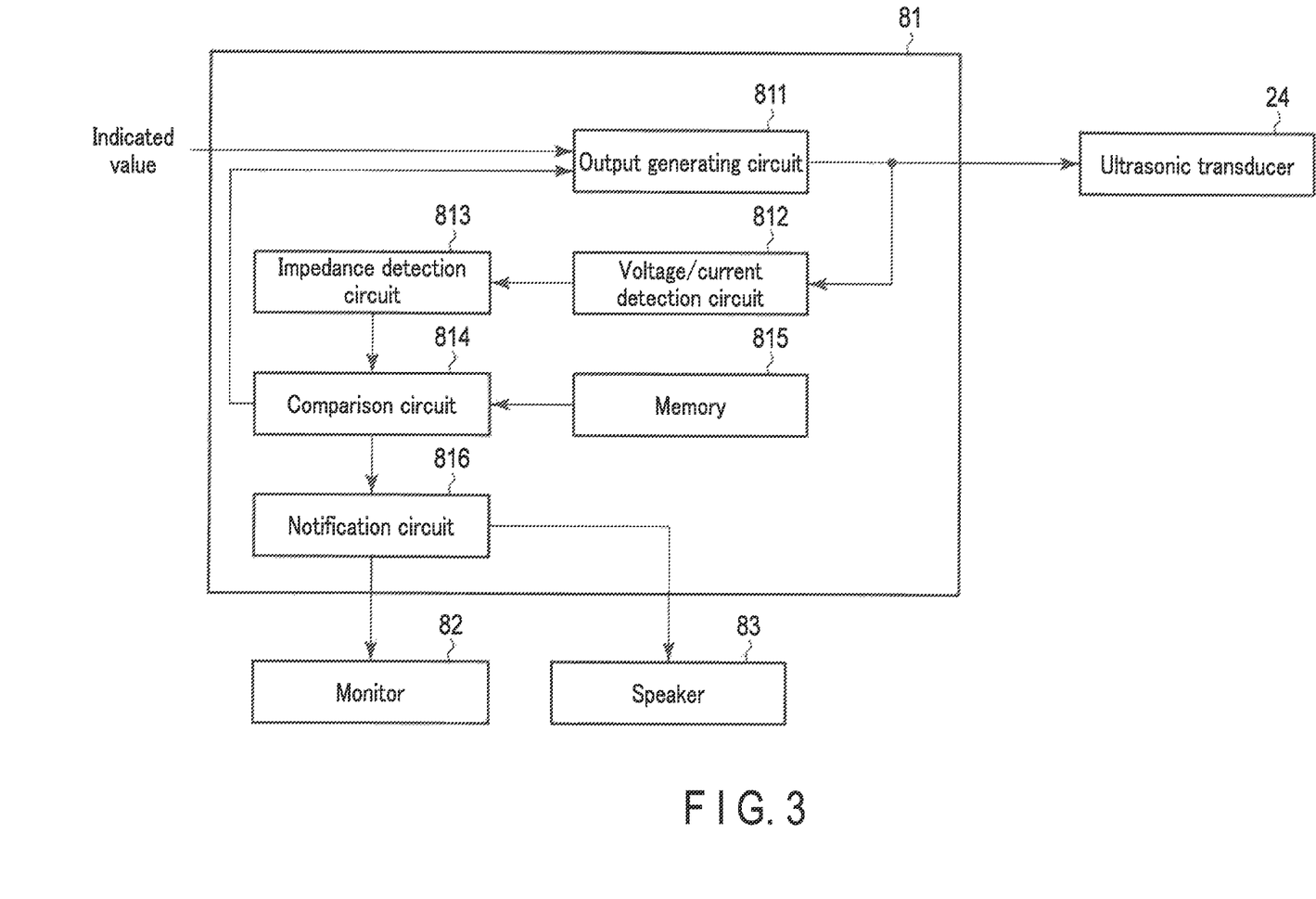
FIG. 3 is a block diagram showing the configuration of a control circuit according to the first embodiment.

FIG. 3 is a block diagram showing the configuration of the control circuit 81 in the first embodiment. The control circuit 81 includes an output generating circuit 811, a voltage/current detection circuit 812, an impedance detection circuit 813, a comparison circuit 814, a memory 815, and a notification circuit 816.

The output generating circuit 811 includes a power supply generation circuit such as a regulator. When the input section 22 or the foot switch 90 is operated, the output generating circuit 811 generates driving power of the ultrasonic transducer 24 so that the ultrasonic transducer 24 vibrates with an amplitude in response to an instructed value from the input section 22 or the foot switch 90.

Comparing an amplitude in the cartilage excision mode with an amplitude in the cortical bone and cancellous bone excision mode, the amplitude in the cartilage excision mode is set to be higher than the amplitude in the cortical bone and cancellous bone excision mode. This is because, in the cartilage excision mode, excision is mainly performed by frictional heat caused by ultrasonic vibration. Here, assuming that the gravitational acceleration is g(m/s$^2$), the quantity of heat Q [J] when an object having a mass m [kg] slides on a coarse horizontal surface having a dynamic friction coefficient μ', the following Equation 1 is given.

$$Q = \mu' mgs \qquad \text{(Equation 1)}$$

In Equation 1, assuming that the pressing force is a vertical component of a force with respect to the rough surface in Equation 1, it can be considered that the magnitude of the pressing force (N) of the probe 180 corresponds to mg in the above equation. Also, s corresponds to the amplitude of the vertical vibration of the ultrasonic probe. Therefore, if the pressing force is constant, the excision amount of the cartilage increases as the amplitude of the probe 180 is increased.

Therefore, in the cartilage excision mode, the amplitude of ultrasonic vibration is set as large as possible in order to improve excision efficiency. On the other hand, in the cortical bone and cancellous bone excision mode, excision is performed by impacts caused by ultrasonic vibration rather than frictional heat by ultrasonic vibration. In a cortical bone and cancellous bone excision mode, frictional heat caused by ultrasonic vibration does not contribute much to excision.

Therefore, the amplitude of the ultrasonic vibration in the cortical bone and cancellous bone excision mode may be set smaller than the amplitude in the cartilage excision mode. Here, the pressing force is taken as the vertical component of the force with respect to the rough surface, but it is of course possible to consider the pressing force as a force in a state having an angle with respect to the verticality, for example.

The voltage/current detection circuit 812 detects an output voltage and an output current of the output generating circuit 811, respectively.

The impedance detection circuit 813 calculates impedance of the ultrasonic transducer 24 from a ratio between an output voltage and an output current detected by the voltage/current detection circuit 812. The impedance of the ultrasonic transducer 24 can be changed by the pressing force of the probe 180 against a living tissue. Therefore, the impedance detection circuit 813 functions as a detection circuit that indirectly detects the pressing force of the probe 180 by detecting the impedance of the ultrasonic transducer 24. The impedance of the ultrasonic transducer 24 can also vary depending on the type and temperature of a living tissue against which the ultrasonic transducer 24 is pressed. Therefore, when a pressing force is calculated from the impedance, it is desirable to correct an impedance value according to the type and temperature of the living tissue. In addition, the influence of the change in the pressing force on the impedance is larger than the influence of the type of the living tissue and the temperature change. Therefore, when a pressing force is calculated from the impedance, the influence of the type and temperature of the living tissue may be ignored.

The comparison circuit 814 converts the value of the impedance detected by the impedance detection circuit 813 into a value of the pressing force. Then, the comparison circuit 814 compares the converted value of the pressing force with the range of pressing forces stored in the memory 815. Then, the comparison circuit 814 instructs the notification circuit 816 to notify according to the comparison result of the pressing force.

The memory 815 has stored the range of pressing forces. As the pressing force decreases, the excision amount decreases, and it takes time for surgery. As the pressing force increases, the excision amount increases but the heat invasion to surrounding tissues also increases. Therefore, the range of pressing forces is determined by the balance between the excision amount and the heat invasion. The range of pressing forces in the cortical bone and cancellous bone excision mode is different from the range of pressing forces used in the cartilage excision mode. The details will be described later. In addition, the memory 815 has stored a table for converting the value of the impedance detected by the impedance detection circuit 813 into a value of the pressing force. This table can be obtained, for example, by actually measuring changes in impedance when the pressing force of the probe 180 is variously changed in a state where the amplitude of the probe 180 is set to a constant value.

The notification circuit 816 notifies the operator by using the monitor 82 and the speaker 83 in accordance with an instruction from the comparison circuit 814. This notification is whether the operator presses the probe 180 appropriately, strongly or weakly. A notification, such as when the pressing force is strong, the user is instructed to decrease the pressing, and when the pressing is weak, the user is instructed to increase the pressing may be performed. Furthermore, the notification, may be performed by displaying a gauge, etc., representing a pressing force.

Figure 4:
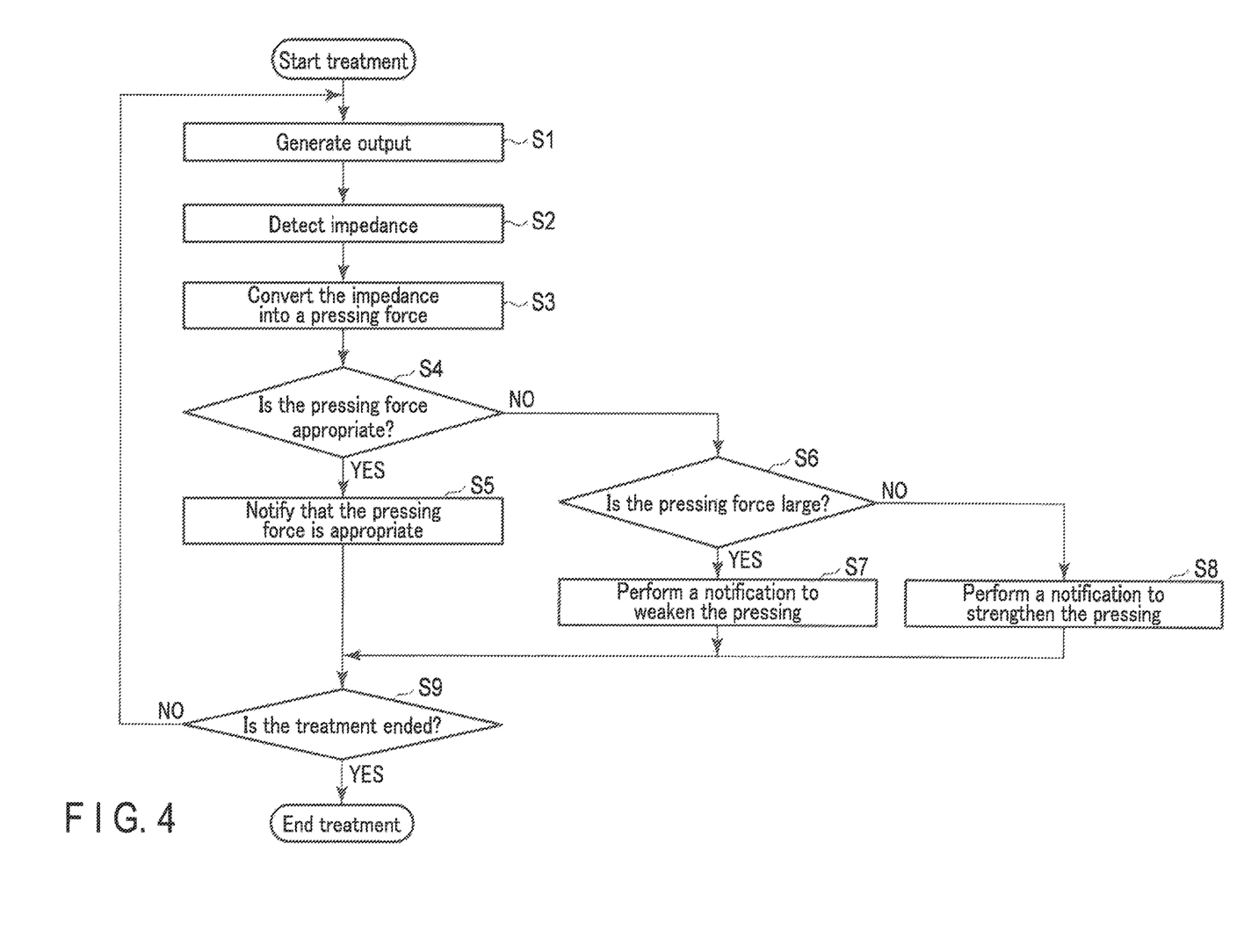
FIG. 4 is a flowchart showing the operation of the ultrasonic surgical system.

Hereinafter, the operation of the ultrasonic surgical system 1 according to the present embodiment will be described. FIG. 4 is a flowchart showing the operation of the ultrasonic surgical system 1. The processing of FIG. 4 is started, for example, when the power of the ultrasonic surgical system 1 is turned on and the input section 22 or the foot switch 90 is operated.

In step S1, the output generating circuit 811 generates driving power for driving the ultrasonic transducer 24. When it is instructed by the input section 22 or the foot switch 90 that the cartilage excision mode is in effect, the output generating circuit 811 generates driving power so that ultrasonic vibration is generated with an amplitude corresponding to a preset instruction value for the cartilage excision mode. On the other hand, when it is instructed by the input section 22 or the foot switch 90 that the cortical bone and cancellous bone excision mode is in effect, the output generating circuit 811 generates driving power so that ultrasonic vibration is generated with an amplitude corresponding to the preset instruction value for the cortical bone and cancellous bone excision mode. The output generating circuit 811 may be configured to perform feedback-control on the driving power. In this case, for example, an output current of the output generating circuit 811 detected by the voltage/current detection circuit 812 is returned to the output generating circuit 811. Then, the output generating circuit 811 controls the output voltage so that the returned output current coincides with the instructed value.

In step S2, the impedance detection circuit 813 calculates impedance of the ultrasonic transducer 24 from a ratio of the output voltage and the output current detected by the voltage/current detection circuit 812.

In step S3, the comparison circuit 814 converts the value of the impedance calculated by the impedance detection circuit 813 into a value of the pressing force in accordance with a table stored in advance in the memory 815.

In step S4, the comparison circuit 814 compares a value of the current pressing force obtained from the value of the impedance with the range of pressing forces stored in advance in the memory 815. Then, based on the comparison result, the comparison circuit 814 determines whether or not the pressing force of the probe 180 by the operator is appropriate. For example, if the value of the current pressing force is within the range of pressing forces stored in advance in the memory 815, it is determined that the pressing force is appropriate.

Figure 5:
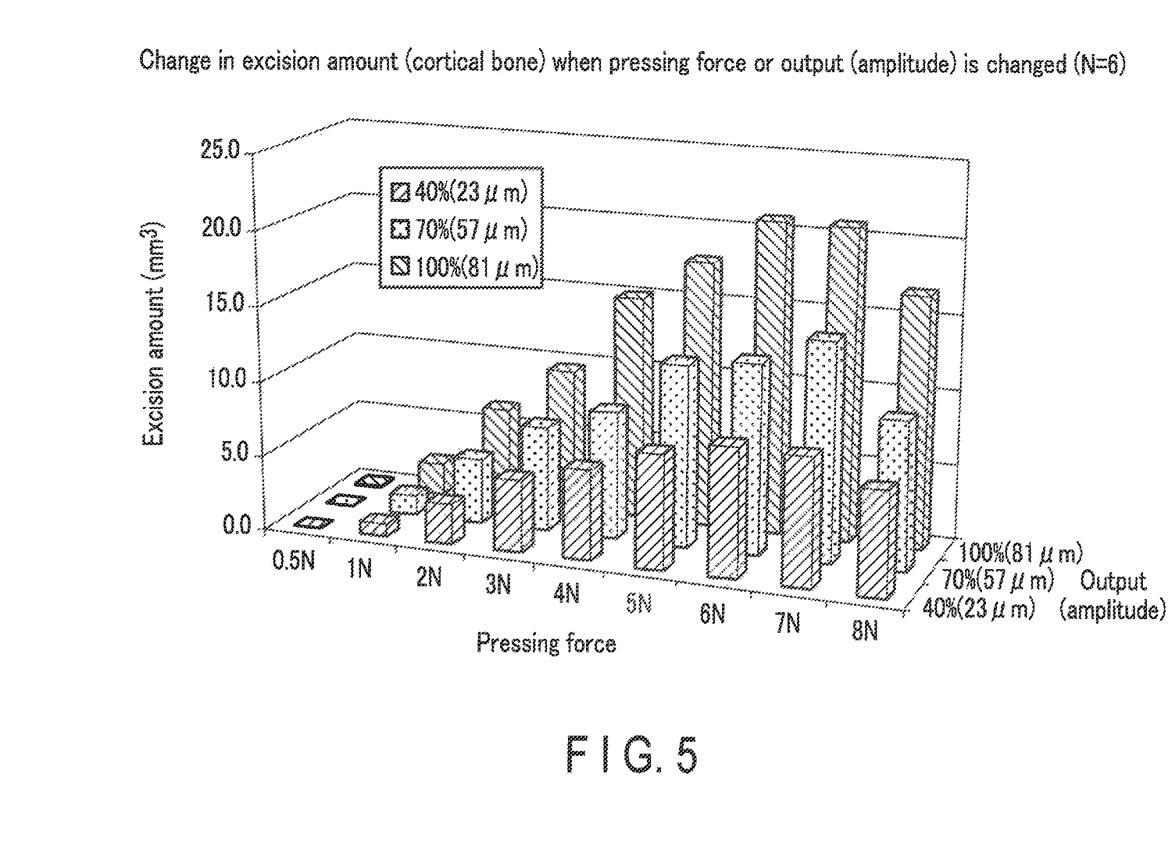
FIG. 5 is a graph showing experimental results of measuring a change in excision amount when a pressing force or an amplitude is changed with respect to cortical bone.

The range of pressing forces will be described below. FIG. 5 is a graph showing experimental results of measuring a change in excision amount when a pressing force or an amplitude is changed with respect to cortical bone. In the experiment, an excision amount (the volume of an excised cortical bone) is measured when a vibration jig capable of changing the pressing force and amplitude is pushed against six points (N=6) of the cortical bone to be measured. In addition, in the graph of FIG. 5, the average value of the excision amounts of six points is shown. Also, the value of the amplitude is indicated as a percentage with respect to the maximum amplitude (81 μm) of the jig used in the experiment.

As shown in FIG. 5, in the case of cortical bone, as an overall tendency, when the pressing force is the same, the larger the amplitude, the larger the excision amount becomes. When the amplitude is the same, the larger the pressing force, the larger the excision amount becomes.

However, when the pressing force is 0.5 (N) or less, even if the amplitude is increased, the excision amount does not increase. Also, when the pressing force exceeds 8(N), the excision amount does not increase, either. As described above, the cortical bone is mainly excised by impacts caused by ultrasonic vibration. Therefore, when the pressing force is too small or too large and the transmission efficiency of the impact due to ultrasonic vibration degrades, the excision amount becomes small. From the graph of FIG. 5, it can be considered that the range of pressing forces in the cortical bone and cancellous bone excision mode is 3(N)-5(N) when the amplitude is 400 (23 µm), when the amplitude is 700 (57 µm), the range of pressing forces is 2(N)-6(N), and when the amplitude is 1000 (81 µm), the range of pressing forces is 1(N)-7(N). These values are stored in the memory 815.

Figure 6A:
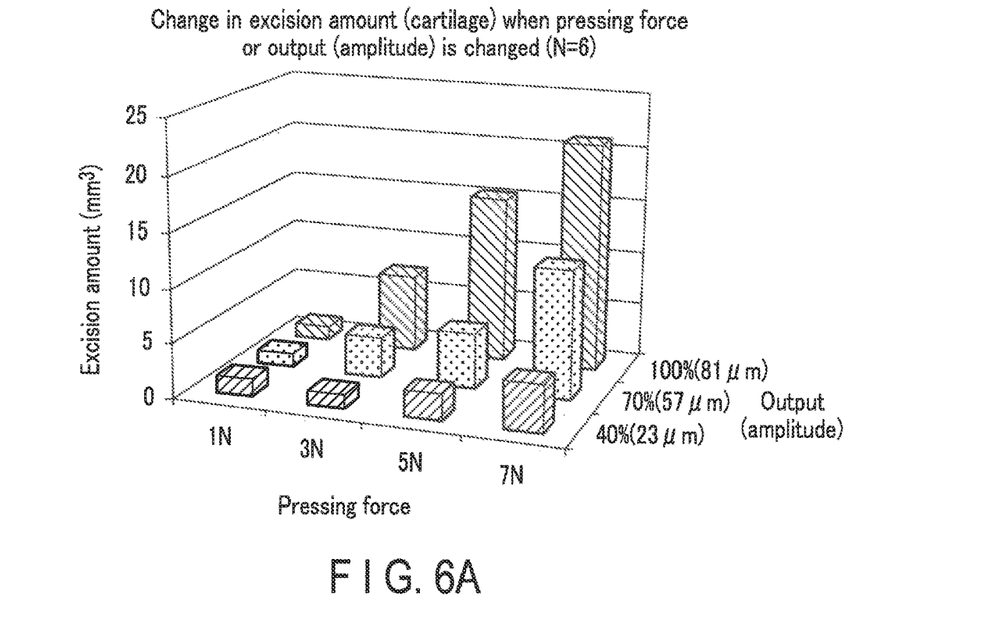
FIG. 6A is a graph showing experimental results of measuring a change in excision amount when a pressing force or an amplitude is changed with respect to a cartilage.

FIG. 6A is a graph showing an experimental result of measuring a change in excision amount when a pressing force or an amplitude is changed on a cartilage. Also in FIG. 6A, the average value of excision amounts (the volume of an excised cortical bone) at six points (N=6) of the cartilage to be measured is shown. Also, the value of the amplitude is indicated as a percentage with respect to the maximum amplitude (81 µm) of the jig used in the experiment.

Figure 6B:
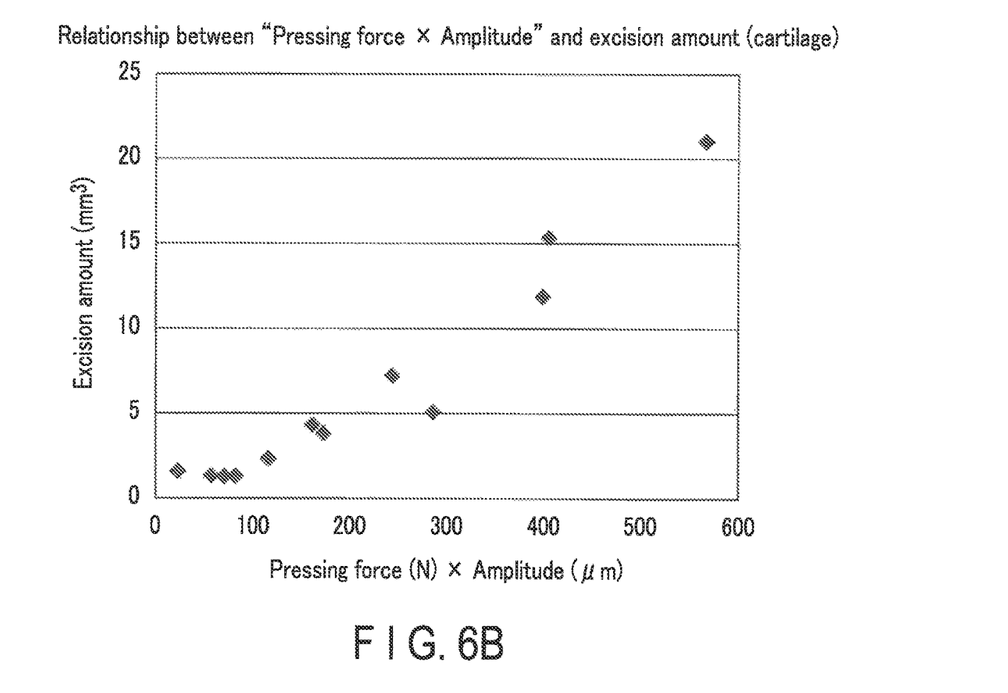
FIG. 6B is a graph in which a value (pressing force)× (amplitude) is taken on the horizontal axis and the excision amounts are taken on the vertical axis based on the results of FIG. 6A.

As shown in FIG. 6A, in the case of a cartilage, as an overall tendency, when the pressing force is the same, the larger the amplitude, the larger the excision amount becomes. When the amplitude is the same, the larger the pressing force, the larger the excision amount becomes. In the case of a cartilage, unlike in the case of cortical bone, at 100 [N·µm] or less, the cartilage does not melt and excision does not proceed. This is because the cartilage is mainly excised by frictional heat caused by ultrasonic vibration. FIG. 6B is a graph in which (pressing force)×(amplitude) is taken on the horizontal axis and an excision amount is taken on the vertical axis based on the result of FIG. 6A. If the value of (pressing force)×(amplitude) (i.e., corresponding to the amount of heat) becomes too large, the amount of excision increases but the heat invasion also increases.

Therefore, for example, the range of pressing forces in the cartilage excision mode is a value when the value of (pressing force)×(amplitude) is set to be 100 [N·µm]-300 [N·µm]. This value is stored in the memory 815.

In this way, the comparison circuit 814 compares the range of pressing forces determined by the relationship shown in FIG. 5 or 6B with the current pressing force. In step S4, when it is determined that the pressing force is appropriate, the processing transfers to step S5. In step S4, if it is determined that the pressing force is not appropriate, the processing transfers to step S6.

In step S5, the comparison circuit 814 notifies the notification circuit 816 that the pressing force is appropriate. Upon receiving this notification, the notification circuit 816 notifies the operator by using the monitor 82 and the speaker 83 that the current pressing by the operator is appropriate. Thereafter, the processing transfers to step S9. The notification is performed, for example, by displaying letters such as "The pressing is appropriate" on the monitor 82, by emitting sound from the speaker 83, or by using both of them.

In step S6, the comparison circuit 814 determines whether or not the pressing force of the probe 180 by the operator is large. For example, when the value of the current pressing force is larger than values in the range of pressing forces stored in advance in the memory 815, it is determined that the pressing force is large. On the other hand, when the value of the current pressing force is smaller than values in the range of pressing forces stored in advance in the memory 815, it is determined that the pressing force is small. In step S6, when it is determined that the pressing force is large, the processing transfers to step S7. In step S6, when it is determined that the pressing is small, the processing transfers to step S8.

In step S7, the comparison circuit 814 notifies the notification circuit 816 that the pressing force is large. Upon receiving this notification, the notification circuit 816 notifies the operator by using the monitor 82 and the speaker 83 to urge the operator to decrease the pressing by the operator. Thereafter, the processing transfers to step S9. The notification is performed, for example, by displaying letters such as "Decrease the pressing" on the monitor 82, by emitting sound from the speaker 83, or by using both of them.

In step S8, the comparison circuit 814 notifies the notification circuit 816 that the pressing force is small. Upon receiving this notification, the notification circuit 816 notifies the operator by using the monitor 82 and the speaker 83 to urge the operator to increase the pressing by the operator. Thereafter, the processing transfers to step S9. The notification is performed, for example, by displaying letters such as "Increase the pressing" on the monitor 82, by emitting sound from the speaker 83, or by using both of them.

In step S9, the output generating circuit 811 determines whether to end the processing. For example, it is determined that the processing should be ended when the power of the ultrasonic surgical system 1 is turned off, or when the operation of the input section 22 or the foot switch 90 is canceled. When it is determined in step S9 that the processing should be ended, the processing of FIG. 4 ends. If it is determined in step S9 that the processing is not to be ended, the process returns to step S1.

As described above, according to the present embodiment, the pressing force of the probe 180 against the living tissue by the operator is compared with a predetermined range of pressing forces, and whether or not the pressing by the operator is appropriate is notified according to the comparison result. With this configuration, the operator can perform a treatment with an appropriate pressing force.

Furthermore, in the present embodiment, the range of pressing forces is differentiated between the cortical bone and cancellous bone excision mode and the cartilage excision mode. With this configuration, the operator can perform the pressing, counting only on a notification from the ultrasonic surgical system 1 without being aware of the difference between the cortical bone and cancellous bone excision mode and the cartilage excision mode.

The processing in each step of FIG. 4 is performed using "circuits", but it may be performed by software.

Modification of First Embodiment

A modification of the first embodiment will be described below. The pressing force described in the first embodiment can also be considered as the magnitude of an output voltage generated by the output generating circuit 811. In the constant current control, when the pressing force becomes large and the load from the living body becomes large, the output generating circuit 811 increases the output voltage so as to make the output current constant. Therefore, the pressing force is substantially proportional to the output voltage generated by the output generating circuit 811. Therefore, instead of a value of the pressing force, a value of the output voltage can be stored in the memory 815. In this case, the impedance detection circuit 813 may be omitted.

Figure 7:
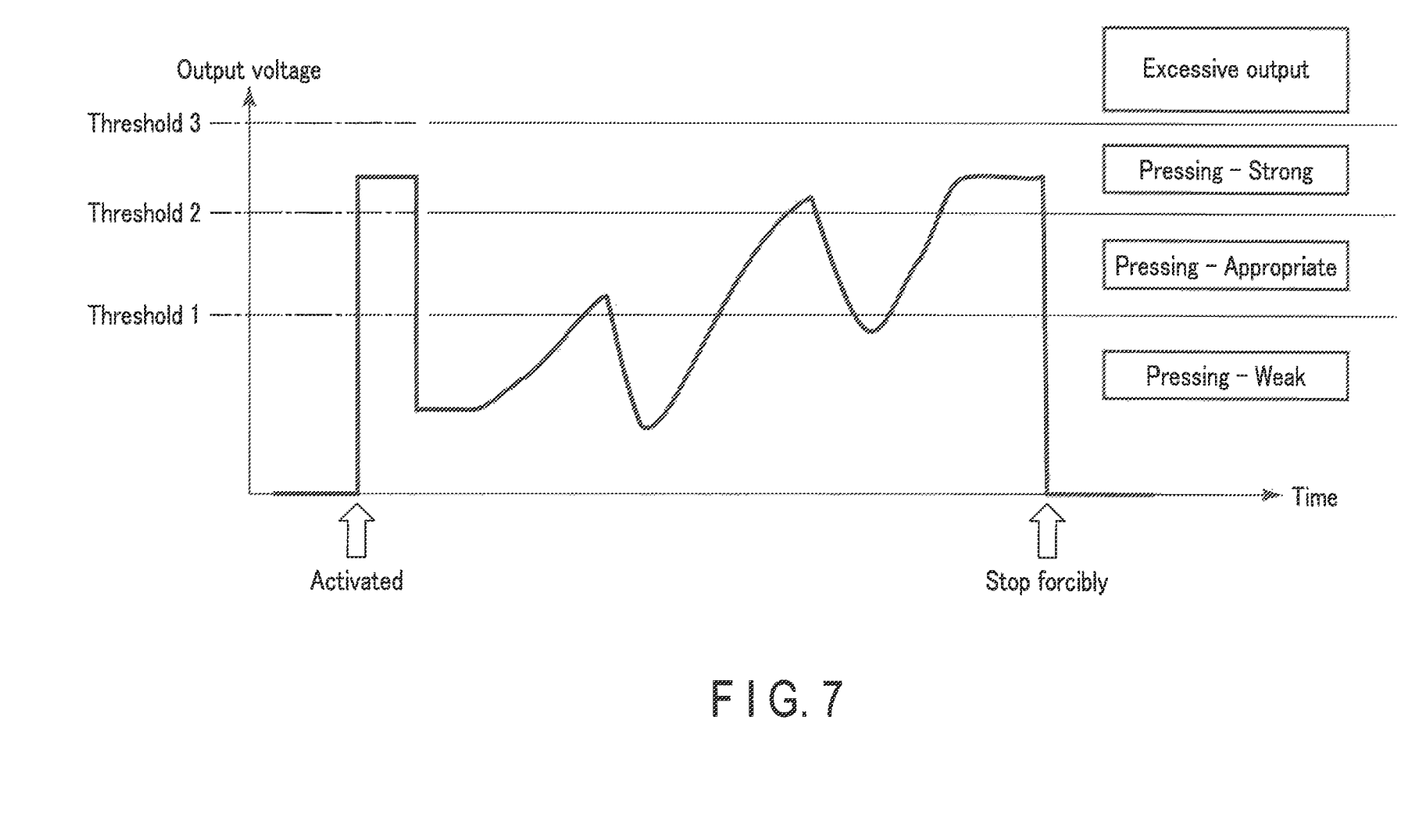
FIG. 7 is a diagram showing a relationship between an output voltage from the start of output of the ultrasonic surgical system and a notification to an operator of the ultrasonic surgical system.

FIG. 7 is a diagram showing the relationship between the output voltage from the start of output of the ultrasonic surgical system 1 and the notification to the operator. Here, the horizontal axis of FIG. 7 shows the time that has passed from the start of output of the ultrasonic surgical system 1. The vertical axis of FIG. 7 shows values of the output voltage. Although FIG. 7 shows an example in the case of cortical bone, it is also possible to notify the operator also in the case of a cartilage by using the output voltage.

In the example of FIG. 7, thresholds of three kinds of output voltages are stored in the memory 815. A threshold 1 is the lower limit value of the output voltage for excision cortical bone. That is, when the output voltage is less than the threshold 1, the pressing force is too weak, so that the transmission efficiency of the impact degrades, and sufficient excision is not performed. For this reason, a notification to urge the operator to increase the pressing is performed.

On the other hand, a threshold 2 is the upper limit value of the output voltage for appropriately excision the cortical bone. The threshold 2 is, for example, 1100 Vpp (voltage amplitude value). That is, when the output voltage exceeds the threshold 2, the pressing force is too strong, so that the transmission efficiency of the impact degrades and sufficient excision is not performed. Also, when the output voltage exceeds the threshold 2, the living tissue may be burned. For this reason, a notification to urge the operator to decrease the pressing is performed. Furthermore, when the output voltage exceeds the threshold 2 for a predetermined time, the operation of the ultrasonic system 1 is forcibly stopped. The threshold 2 may be a rated voltage of the output generating circuit 811.

Furthermore, a threshold 3 is a value determined by the power supply restriction of the output generating circuit 811. In a state where the output voltage has reached the threshold 3, the output generating circuit 811 cannot generate any more voltage, and it is considered that the ultrasonic surgical system 1 is performing an abnormal operation. In this case, it is desirable not only to perform the notification, but also to forcibly stop the operation of the ultrasonic surgical system 1.

Figure 8:
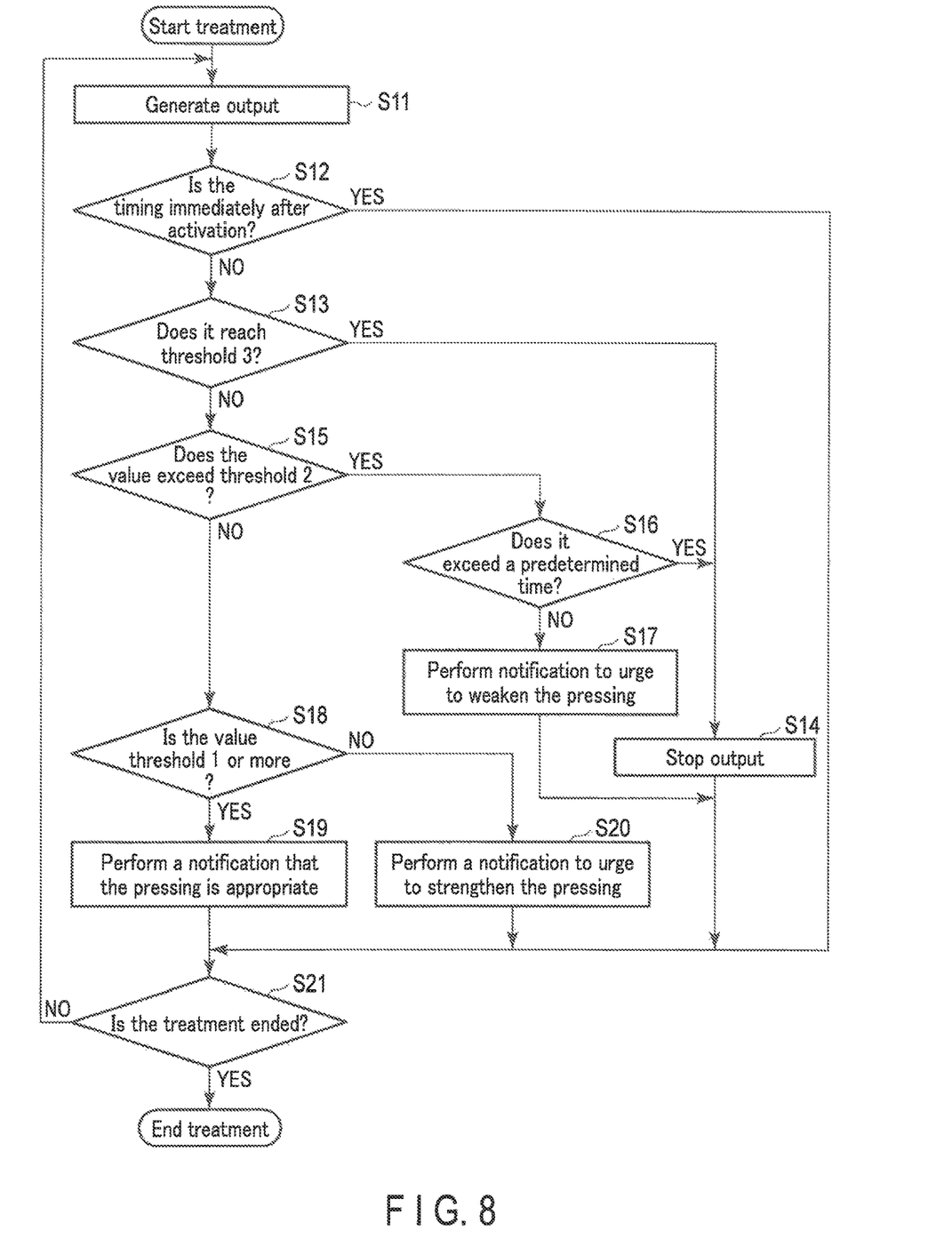
FIG. 8 is a flowchart showing the operation of a modification of the ultrasonic surgical system.

FIG. 8 is a flowchart showing the operation of the ultrasonic surgical system 1 according to the modification. The processing of FIG. 8 is started, for example, when the power of the ultrasonic surgical system 1 is turned on and the input section 22 or the foot switch 90 is operated. The operation of FIG. 8 can also be applied to the case where the pressing force is compared with the threshold as in the first embodiment.

In step S11, the output generating circuit 811 generates driving power for driving the ultrasonic transducer 24. When it is instructed by the input section 22 or the foot switch 90 that the cartilage excision mode is in effect, the output generating circuit 811 generates driving power so that ultrasonic vibration is generated with an amplitude corresponding to a preset instruction value for the cartilage excision mode. On the other hand, when it is instructed by the input section 22 or the foot switch 90 that the cortical bone and cancellous bone excision mode is in effect, the output generating circuit 811 generates driving power so that ultrasonic vibration is generated with an amplitude corresponding to a preset instruction value for the cortical bone and cancellous bone excision mode.

In step S12, the comparison circuit 814 determines whether or not it is the timing immediately after activation of the ultrasonic surgical system 1. The timing immediately after activation here is the timing immediately after the start of the output of the output voltage in the ultrasonic surgical system 1. As shown in FIG. 7, a large output voltage is instantaneously generated at the timing (about 500 ms) immediately after the start of output of the output voltage of the ultrasonic surgical system 1. In order not to erroneously determine such an instantaneous large voltage as an increase in pressing pressure, the processing of steps S13 to S20 is not performed immediately after the activation of the ultrasonic surgical system 1. In step S12, when it is determined that the timing is immediately after activation of the ultrasonic surgical system 1, the processing transfers to step S21. When it is determined in step S12 that the timing is not immediately after activation of the ultrasonic surgical system 1, the processing transfers to step S13.

In step S13, the comparison circuit 814 compares the value of the current output voltage detected by the voltage/current detection circuit 812 with the threshold of the output voltage stored in advance in the memory 815. Then, the comparison circuit 814 determines whether or not the value of the current output voltage has reached the threshold 3. In step S13, when it is determined that the value of the current output voltage has reached the threshold 3, the processing transfers to step S14. In step S13, when it is determined that the value of the current output voltage has not reached the threshold 3, the processing transfers to step S15.

In step S14, the comparison circuit 814 requests the output generating circuit 811 to stop the generation of the output voltage. Upon receiving this request, the output generating circuit 811 stops the generation of the output voltage. Thereafter, the processing transfers to step S21. In step S14, it may be configured to notify the operator that the operation of the ultrasonic surgical system 1 has stopped.

In step S15, the comparison circuit 814 determines whether or not the value of the current output voltage exceeds the threshold 2. In step S15, when it is determined that the value of the current output voltage exceeds the threshold 2, the processing transfers to step S16. In step S15, when it is determined that the value of the current output voltage has not exceeded the threshold 2, the processing transfers to step S18.

In step S16, the comparison circuit 814 determines whether or not a predetermined time (e.g., 3 seconds) has passed after the value of the current output voltage has exceeded the threshold 2. In step S16, when it is determined that the predetermined time (e.g., 3 seconds) has passed after the value of the current output voltage has exceeded the threshold 2, the processing transfers to step S14. That is, when the value of the current output voltage has exceeded the threshold 2 for the predetermined time, the generation of the output voltage is stopped. In step S16, when it is determined that the predetermined time (e.g., 3 seconds) has not passed after the value of the current output voltage has exceeded the threshold 2, the processing transfers to step S17.

In step S17, the comparison circuit 814 notifies the notification circuit 816 that the pressing force is large. Upon receiving this notification, the notification circuit 816 notifies the operator by using the monitor 82 and the speaker 83 to urge the operator to decrease the pressing by the operator. Thereafter, the processing transfers to step S21. The notification is performed, for example, by displaying letters such as "Decrease the pressing" on the monitor 82, by emitting sound from the speaker 83, or by using both of them. That is, if the output voltage is increased for a short time, only a notification is performed without forcibly stopping the ultrasonic surgical system 1. The notification may be performed by changing the phonetic pattern of a specific sound instead of sound.

In step S18, the comparison circuit 814 determines whether or not the value of the current output voltage is equal to or larger than the threshold 1. In step S18, when it is determined that the value of the current output voltage is equal to or larger than the threshold 1, the processing transfers to step S19. In step S18, when it is determined that the value of the current output voltage is not equal to or larger than the threshold 1, the processing transfers to step S20.

In step S19, the comparison circuit 814 notifies the notification circuit 816 that the pressing force is appropriate. Upon receiving this notification, the notification circuit 816 notifies the operator by using the monitor 82 and the speaker 83 that the current pressing by the operator is appropriate. Thereafter, the processing transfers to step S21. The notification is performed, for example, by displaying letters such as "The pressing is appropriate" on the monitor 82, by emitting sound from the speaker 83, or by using both of them. When the pressing force is appropriate, the notification may not be performed. Furthermore, the notification may be performed by changing the phonetic pattern of a specific sound instead of sound.

In step S20, the comparison circuit 814 notifies the notification circuit 816 that the pressing force is small. Upon receiving this notification, the notification circuit 816 notifies the operator by using the monitor 82 and the speaker 83 to urge the operator to increase the pressing. Thereafter, the processing transfers to step S21. The notification is performed, for example, by displaying letters such as "Increase the pressing" on the monitor 82, by emitting sound from the speaker 83, or by using both of them. The notification may be performed by changing the phonetic pattern of a specific sound instead of sound.

In step S21, the output generating circuit 811 determines whether to end the processing. For example, it is determined that the processing should be ended when the power of the ultrasonic surgical system 1 is turned off, or when the operation of the input section 22 or the foot switch 90 is canceled. In step S21, when it is determined that the processing should be ended, the processing of FIG. 8 ends. In step S21, when it is determined that the processing is not to be ended, the processing returns to step S11.

The above-described modification enables determination on the pressing force similar to that in the first embodiment by regarding the output voltage as a pressing force, without directly detecting the pressing force. That is, also in this modification, the operator can perform a treatment with an appropriate pressing force.

In the modification, basically, an instantaneous value of the output voltage is compared with the threshold. In contrast, instead of an instantaneous value of the output voltage, an average value, an accumulated value, a most frequent value, a maximum value, etc. of the output voltage within a certain period of time may be compared with the threshold. It is possible to configure the modification so that a moving average value, an accumulated value, a most frequent value, or a maximum value of the output voltage for a certain period of time is compared with the threshold without performing a notification by an instantaneous change in the output voltage. With this configuration, notification beyond necessity is suppressed. Furthermore, when a moving average value, an accumulated value, a most frequent value, or a maximum value is compared with the threshold, the modification may be configured to perform a notification when each of the moving average value, accumulated value, most frequent value, and maximum value exceeds the threshold 2 or becomes less than the threshold 1 for a certain period of time. For example, in the case of a moving average value or an accumulated value, the value is leveled information as it is, but in consideration of the influence of noise, the modification may be configured to perform a notification when a state where the value exceeds the threshold 2, or where the value being less than the threshold 1 is maintained for a certain period of time. In the case of a maximum value, there is a concern of noise, etc. as compared with the case of a moving average value. For this reason, the modification may be configured to perform a notification when the value exceeds the threshold 2 or is less than the threshold 1 for at least half of the predetermined period of time. Furthermore, in the case of a most frequent value, since the value is considered information in which the pressing force is sufficiently reflected, the modification may be configured to perform a notification when the value exceeds the threshold 2 or becomes less than the threshold 1 for a certain period of time.

Also, the way of notifying may be changed depending on how the output voltage changes. For example, even when the output voltage has exceeded the threshold 2, it is considered that the output voltage will eventually fall below the threshold 2 without performing a notification, if the output voltage tends to decrease. Based on such a concept, for example, the way of notifying may be replaced by a configuration in which a notification is performed to urge to decrease the pressing only when the output voltage tends to increase, without performing a notification to urge to decrease the pressing when the output voltage tends to decrease even if the output voltage has exceeded the threshold 2. Likewise, for example, the way of notifying may be replaced by a configuration in which even if the output voltage is less than the threshold 1, a notification to urge to increase the pressing is not performed when the output voltage tends to increase, and a notification to urge to increase the pressing is performed only when the output voltage tends to decrease.

Furthermore, when an average value, an accumulated value, a most frequent value, a maximum value, etc. of the output voltage within a certain period of time is compared with the threshold, instead of using an instantaneous output voltage, the length of a certain period of time during which a notification is performed may be changed depending on the way of changing the output voltage. For example, the length of the certain period of time, when the output voltage has exceeded the threshold 2 and the output voltage tends to increase, may be shorter than the length of the certain period of time when the output voltage has exceeded the threshold 2 and the output voltage tends to decrease. With this configuration, when the output voltage tends to increase, which should be notified more urgently, the notification is performed promptly.

Furthermore, in the present modification, different notifications are performed in response to the three thresholds; however, the number of thresholds is not limited to three. For example, a notification may be performed using two thresholds, i.e., threshold 1 and threshold 2, or in response to four or more thresholds.

Second Embodiment

Hereinafter, a second embodiment of the present invention will be described. In the first embodiment, a current pressing force is compared with a range of pressing forces to perform a notification to the operator in accordance with a comparison result. In contrast, in the second embodiment, a current pressing force is compared with a range of pressing amounts to perform feedback-control of the amplitude of the ultrasonic transducer 24 in accordance with a comparison result.

Figure 9:
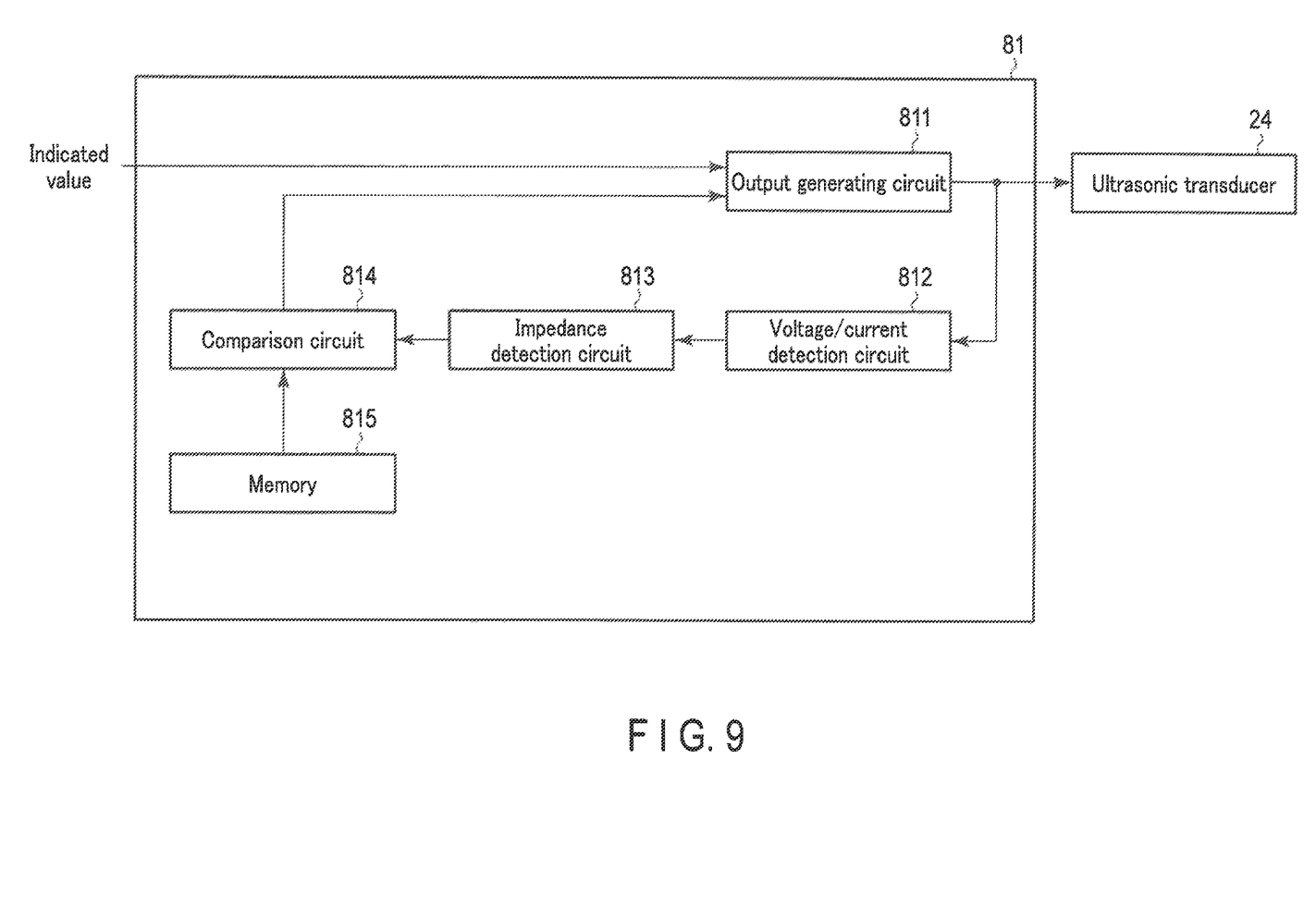
FIG. 9 is a block diagram showing the configuration of a control circuit according to the second embodiment.

FIG. 9 is a block diagram showing the configuration of a control circuit 81 in the second embodiment. The control circuit 81 includes an output generating circuit 811, a voltage/current detection circuit 812, an impedance detection circuit 813, a comparison circuit 814, and a memory 815. The control circuit 81 in the second embodiment is configured so that an output of the comparison circuit 814 is returned to the output generating circuit 811.

Similar to the output generating circuit 811 in the first embodiment, the output generating circuit 811 in the second embodiment controls the driving power so that ultrasonic vibrations having different amplitudes are generated between the cortical bone and cancellous bone excision mode and the cartilage excision mode. Furthermore, in the cartilage excision mode, the output generating circuit 811 in the second embodiment performs control so as to increase or decrease the amplitude in response to a difference between a value of the current pressing force and the upper limit value or the lower limit value in the range of pressing forces stored in advance in the memory 815. For example, the output generating circuit 811 performs control so as to increase or decrease the amplitude so that the value of the current pressing force is set to a value of (pressing force)× (amplitude) satisfying the condition of 100[N·μm]–300 [N·μm]. Furthermore, in the cortical bone/cancellous bone excision mode, the output generating circuit 811 performs control so as to increase or decrease the amplitude in accordance with a value of the current pressing force. For example, when the pressing force is 3N or less, the output generating circuit 811 performs control so as to increase the amplitude in order to suppress a decrease in the excision amount. When the pressing force is 5N or more, the output generating circuit 811 performs control so as to decrease the amplitude as a safety measure for suppressing generation of heat.

As described above, according to the present embodiment, the feedback control of the amplitude is performed in accordance with a difference between a value of the current pressing force and the upper limit value or the lower limit value of the range of pressing forces stored in advance in the memory 815. Therefore, the operator can perform a treatment without changing the strength of the pressing.

Similar to the modification of the first embodiment, the pressing force may be detected as an output voltage of the output generating circuit 811. In this case, the impedance detection circuit 813 may be omitted.

Third Embodiment

Figure 10:
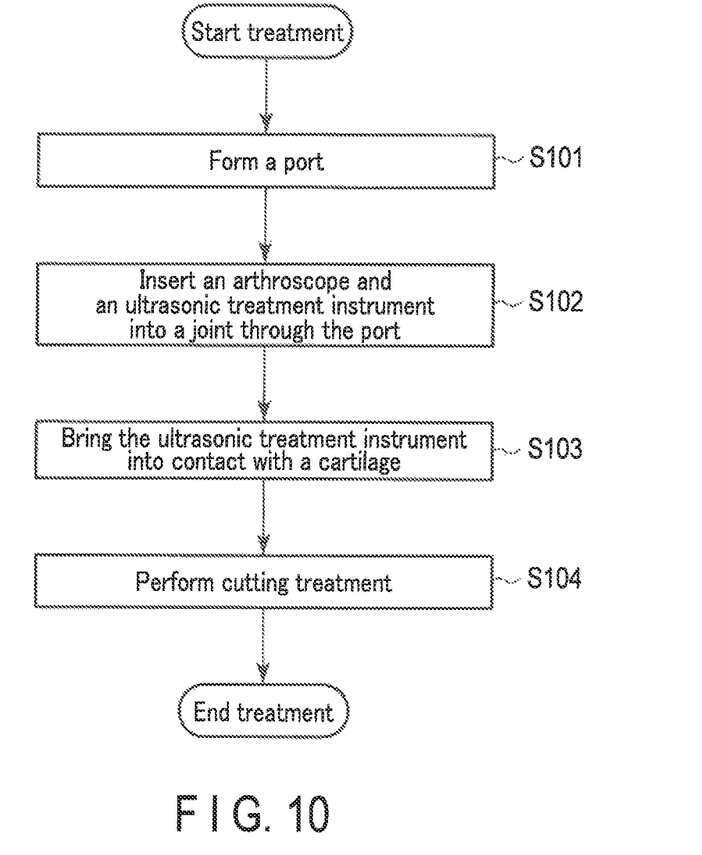
FIG. 10 is a flowchart showing a flow of treatment using the ultrasonic surgical system.

Hereinafter, a third embodiment of the present invention will be described. The third embodiment is a treatment method using the ultrasonic surgical system of the present embodiment. FIG. 10 is a flowchart showing a flow of a treatment using an ultrasonic surgical system 1. FIG. 10 shows the flow of an excision treatment of a degenerative cartilage in a knee joint. The flow shown in FIG. 10 is applicable not only to knee joints, but also to other joints such as shoulder joints.

In step S101, a doctor uses a trocar to form a port through which a treatment instrument and an arthroscope can be inserted to the position of a living tissue to be treated (in this case, a degenerative cartilage in the knee joint).

In step S102, the doctor inserts the arthroscope and a treatment instrument 10 of the ultrasonic surgical system 1 into the knee joint through the arthroscope port.

In step S103, the doctor brings a treatment section 181 of the ultrasonic surgical system 1 into contact with the degenerative cartilage as a treatment target while observing an image in the knee joint displayed on a monitor through the arthroscope.

In step S104, the doctor operates, for example, an input section 22 to set the ultrasonic surgical system 1 to be in a cartilage melting mode, and while pressing the treatment instrument against the degenerated cartilage, the doctor cuts the degenerative cartilage while checking the degree of pressing of the treatment instrument. At this time, in the case where the pressing by the doctor is strong, for example, "the pressing is too strong" indicating that the pressing is strong is displayed on a monitor 82, and therefore, the doctor decreases the pressing while looking at the monitor 82 and continues the treatment without stopping his or her hand. As a result, when the pressing becomes an appropriate amount, for example, "the pressing is appropriate" is displayed on the monitor 82, and therefore, the doctor performs the treatment while looking at the monitor 82 and maintaining the current pressing degree. On the other hand, if the pressing by the doctor is weak, for example, "Decrease the pressing" is displayed on the monitor 82 indicating that the pressing is weak, and therefore, the doctor increases the pressing while looking at the monitor 82 and continues the treatment without stopping his or her hand. As a result, when the pressing amount becomes an appropriate amount, for example, "the pressing is appropriate" is displayed on the monitor 82, and therefore, the doctor performs the treatment while looking at the monitor 82 and maintaining the current pressing state.

As described above, according to the present embodiment, the doctor can intuitively ascertain whether the treatment is in a state where the excision amount is small due to excessively weak pressing, or whether the treatment is proceeding in a state where heat invasion to surrounding tissues is present because the surgical instrument is excessively pressed against the treatment target, by means of sound or displaying on a monitor, and therefore the doctor can perform safe surgery efficiently with less heat invasion, without stopping his or her hand.

In addition, in the case of using the system according to the second embodiment, the doctor can proceed with a surgery without worrying about the pressing force.

Although the present invention has been described based on the above embodiments, the present invention is not limited to the above-described embodiments, and it goes without saying that various modifications and applications are of course possible within the scope of the gist of the present invention. For example, in each of the above-described embodiments, the pressing force is detected based on the impedance of the ultrasonic transducer. However, the pressing force may be detected from those other than the impedance of the ultrasonic transducer. For example, the pressing force may be detected by a sensor that directly detects a force such as a strain gauge. In addition to this, the pressing force may be detected from a change in the resonance frequency of a probe. The pressing force may be detected from the temperature.

A technique of identifying the state of a living tissue from the impedance of an ultrasonic transducer is also known. This technique may be applied to each of the above-described embodiments. In this case, a range of pressing forces corresponding to the identified living tissue is selected.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic surgical instrument comprising:
an ultrasonic transducer configured to vibrate ultrasonically;
a probe configured to treat a living tissue by the ultrasonic vibration;
a detector configured to detect a pressing force of the probe against the living tissue;
a memory configured to store a predetermined value related to a product of a pressing force when the living tissue is a cartilage and an amplitude of the vibration of the ultrasonic transducer;
a comparing circuit configured to compare the pressing force detected by the detector with the predetermined value stored in the memory; and
a notification circuit configured to perform a notification in response to a comparison result obtained by the comparing circuit,
wherein a lower limit value of the predetermined value is 100 (N·µm), which is a value at which the cartilage is melted to excise, and an upper limit value of the predetermined value is 300 (N·µm), which is a value at which heat invasion due to frictional heat is suppressed.

2. The ultrasonic surgical instrument according to claim 1, wherein the predetermined value, when the living tissue is not a cartilage, is 3(N) or more and 5(N) or less.

3. The ultrasonic surgical instrument according to claim 1, wherein the notification circuit is configured to:
notify an operator of the ultrasonic surgical instrument so as to decrease the pressing of the probe against the living tissue when the pressing force detected by the detector is larger than the predetermined value,
notify the operator of the ultrasonic surgical instrument so as to increase the pressing of the probe against the living tissue when the pressing force detected by the detector is smaller than the predetermined value, and
notify the operator of the ultrasonic surgical instrument that the pressing of the probe against the living tissue is appropriate when the pressing force detected by the detector is equal to the predetermined value.

4. The ultrasonic surgical instrument according to claim 1, wherein the notification circuit performs the notification by at least one of sound and display.

5. The ultrasonic surgical instrument according to claim 1, wherein the detector is configured to detect the pressing force based on impedance of the ultrasonic transducer.

6. An ultrasonic surgical instrument comprising:
an ultrasonic transducer configured to vibrate ultrasonically;
a probe configured to treat a living tissue by the ultrasonic vibration;
a detector configured to detect a pressing force of the probe against the living tissue;
a memory configured to store a predetermined value related to a product of a pressing force when the living tissue is a cartilage and an amplitude of the vibration of the ultrasonic transducer; and
an output generating circuit configured to control the amplitude of the ultrasonic vibration generated by the ultrasonic transducer so that the pressing force detected by the detector becomes a predetermined value of a pressing force in accordance with the living tissue,
wherein a lower limit value of the predetermined value is 100 (N·µm), which is a value at which the cartilage is melted to excise, and an upper limit value of the predetermined value is 300 (N·µm), which is a value at which heat invasion due to frictional heat is suppressed.

7. The ultrasonic surgical instrument according to claim 6, wherein the output generating circuit is configured, when a site of a subject against which the probe is pressed is cortical bone or cancellous bone, to increase the amplitude of the ultrasonic vibration if the pressing force detected by the detector is 3N or less, and to control the amplitude of the ultrasonic vibration to be decreased if the pressing force detected by the detector is 5N or more.

8. The ultrasonic surgical instrument according to claim 6, wherein the detector is configured to detect the pressing force based on impedance of the ultrasonic transducer.

9. The ultrasonic surgical instrument according to claim 6, further comprising:
a comparing circuit configured to compare the pressing force detected by the detector with the predetermined value stored in the memory,
wherein the comparing circuit is configured to make a request to the output generating circuit for forcibly stopping driving of the ultrasonic transducer in response to a comparison result.

10. The ultrasonic surgical instrument according to claim 9, wherein the comparing circuit is configured to determine that the ultrasonic transducer is abnormally operating, when the pressing force detected by the detector is larger than a value for detecting an abnormal operation stored in the memory, and to make a request to the output generating circuit for forcibly stopping driving of the ultrasonic transducer.

11. The ultrasonic surgical instrument according to claim 9, wherein the comparing circuit is configured to determine that heat invasion occurs, when a predetermined time has passed after a state where the pressing force detected by the detector is larger than the predetermined value stored in the memory, and to make a request to the output generating circuit for forcibly stopping driving of the ultrasonic transducer.

* * * * *